US012599384B2

(12) United States Patent
Goel et al.

(10) Patent No.: US 12,599,384 B2
(45) Date of Patent: Apr. 14, 2026

(54) OCCLUSION DEVICES AND METHODS OF USE THEREOF

(71) Applicant: Bard Peripheral Vascular, Inc., Franklin Lakes, NJ (US)

(72) Inventors: Emily A. Goel, Phoenix, AZ (US); Logan J. Grace, Tempe, AZ (US); Jeffrey Wang, Phoenix, AZ (US); Oleg Stanilevskiy, Chandler, AZ (US); Michaella Kavanagh, Scottsdale, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 141 days.

(21) Appl. No.: 18/726,258

(22) PCT Filed: Jan. 19, 2022

(86) PCT No.: PCT/US2022/012897
§ 371 (c)(1),
(2) Date: Jul. 2, 2024

(87) PCT Pub. No.: WO2023/140833
PCT Pub. Date: Jul. 27, 2023

(65) Prior Publication Data
US 2025/0072899 A1 Mar. 6, 2025

(51) Int. Cl.
*A61B 17/12* (2006.01)
*A61B 17/00* (2006.01)
(52) U.S. Cl.
CPC .. *A61B 17/12009* (2013.01); *A61B 17/12045* (2013.01); *A61B 17/12172* (2013.01); *A61B 2017/00867* (2013.01)

(58) Field of Classification Search
CPC ........ A61B 17/12009; A61B 17/12045; A61B 17/12109; A61B 17/12131;
(Continued)

(56) References Cited

U.S. PATENT DOCUMENTS

| | | | |
|---|---|---|---|
| 5,284,488 A | 2/1994 | Sideris | |
| 5,944,738 A | 8/1999 | Amplatz | |

(Continued)

FOREIGN PATENT DOCUMENTS

| | | |
|---|---|---|
| CN | 108158621 A | 6/2018 |
| CN | 110507373 A | 11/2019 |
| WO | 2008071952 A2 | 6/2008 |

OTHER PUBLICATIONS

International Search Report and Written Opinion dated Sep. 22, 2022 pertaining to PCT/US22/12897 filed Jan. 19, 2022.

*Primary Examiner* — Ryan J. Severson
(74) *Attorney, Agent, or Firm* — Dinsmore & Shohl LLP

(57) ABSTRACT

Embodiments herein are directed to an occlusion device that includes a body, a pair of lobes, and an adjustment assembly. One of the pair of lobes positioned at a distal portion of the body and the other one is positioned at a proximal portion. The body includes an adjustment assembly positioned between the distal and the proximal portions to change a distance between the pair of lobes. The adjustment assembly includes a receiving member and an elongated member. The elongated member is configured to move the body between an extended position and a retracted position, such that in the retracted position, the elongated member is received within an inner diameter of the receiving member. In the extended position, the elongated member is extended away from a first end of the receiving member such that the distance between the pair of lobes is increased.

20 Claims, 7 Drawing Sheets

(58) Field of Classification Search
CPC .... A61B 17/12172; A61B 2017/00867; A61B
2017/12095; A61B 2090/3966
See application file for complete search history.

(56) References Cited

U.S. PATENT DOCUMENTS

| | | | |
|---|---|---|---|
| 6,022,336 | A * | 2/2000 | Zadno-Azizi ... A61M 25/10184 |
| | | | 604/27 |
| 6,066,149 | A * | 5/2000 | Samson ............... A61B 17/221 |
| | | | 606/127 |
| 8,109,946 | B2 | 2/2012 | Cahill |
| 8,162,974 | B2 | 4/2012 | Eskuri |
| 8,562,643 | B2 | 10/2013 | Tekulve |
| 8,777,974 | B2 * | 7/2014 | Amplatz .......... A61B 17/12159 |
| | | | 606/200 |
| 8,828,051 | B2 | 9/2014 | Javois |
| 9,179,920 | B2 | 11/2015 | Ren |
| 9,307,997 | B2 | 4/2016 | Conder |
| 9,993,252 | B2 | 6/2018 | Keeley |
| 10,092,295 | B2 | 10/2018 | Thuren |
| 10,111,670 | B2 * | 10/2018 | Lorenzo .......... A61B 17/12168 |
| 11,304,701 | B2 * | 4/2022 | Lubock ............. A61B 17/1214 |
| 12,290,266 | B2 * | 5/2025 | Dasnurkar ....... A61B 17/00491 |
| 12,364,615 | B2 * | 7/2025 | Walzman .......... A61M 25/0097 |
| 12,396,732 | B2 * | 8/2025 | Oslund ............ A61B 17/12145 |
| 2002/0143349 | A1 * | 10/2002 | Gifford, III ...... A61B 17/12186 |
| | | | 606/151 |
| 2009/0281567 | A1 | 11/2009 | Osypka |
| 2010/0131007 | A1 | 5/2010 | Figulla |
| 2011/0208234 | A1 | 8/2011 | Mazzocchi |
| 2012/0022572 | A1 | 1/2012 | Braun |
| 2014/0018848 | A1 | 1/2014 | Kladakis |
| 2015/0374483 | A1 * | 12/2015 | Janardhan ............... A61M 1/87 |
| | | | 606/200 |
| 2016/0317158 | A1 * | 11/2016 | Lorenzo .......... A61B 17/12022 |
| 2017/0007260 | A1 * | 1/2017 | O'Brien .......... A61B 17/12145 |
| 2017/0304042 | A1 | 10/2017 | Ren |
| 2018/0092634 | A1 | 4/2018 | Callaghan |
| 2018/0353163 | A1 | 12/2018 | Rafiee |
| 2019/0046210 | A1 | 2/2019 | Bowman |
| 2019/0142406 | A1 | 5/2019 | Amplatz |
| 2020/0138450 | A1 | 5/2020 | Greene, Jr. |
| 2023/0190294 | A1 * | 6/2023 | Dasnurkar ....... A61B 17/12186 |
| | | | 604/509 |
| 2023/0355416 | A1 * | 11/2023 | Walzman ................. A61F 2/95 |
| 2025/0072899 | A1 * | 3/2025 | Goel ............... A61B 17/12009 |

* cited by examiner

OCCLUSION DEVICES AND METHODS OF USE THEREOF

This application is a U.S. national phase of International Application No. PCT/US2022/012897, filed Jan. 19, 2022, which is incorporated herein by reference in its entirety.

TECHNICAL FIELD

The present specification generally relates to occlusion devices and, more specifically, to occlusion devices that are adjustable to match a diameter and a length of a target area of a blood vessel to be occluded.

BACKGROUND

Vascular occlusion or embolization devices are intravascular implants that are intended to occlude blood flow in percutaneous interventions. For example, a vascular occlusion device may be positioned to control hemorrhaging due to aneurysms, certain tumors, and arteriovenous malformations. Vascular occlusion devices may also be positioned to block blood vessels providing flow to certain types of tumors. Existing embolization devices may include helically-wound coils extending lengthwise through a portion of a vessel. Such helical coil-based structures may lack structural support elements to provide adjustability in an axial direction and a radial direction within a target area.

Accordingly, a need exists for an occlusion device that has an adjustable length in the axial direction such that the length of the device may be tailored to the anatomy of the patient.

SUMMARY

In one aspect, an occlusion device is provided. The occlusion device includes a body, a pair of lobes, and an adjustment assembly. The body includes a distal portion and a proximal portion. One of the pair of lobes positioned at the distal portion of the body and the other one of the pair of lobes is positioned at the proximal portion of the body. The body includes an adjustment assembly positioned between the distal portion and the proximal portion to change a distance between the pair of lobes. The adjustment assembly includes a receiving member and an elongated member. The receiving member includes a first end, an opposite second end and an inner diameter. The second end has a flange that extends radially inward into the inner diameter. The elongated member includes a first terminating end, an opposing second terminating end and an outer diameter. The first terminating end has a protrusion that extends radially outward from the outer diameter. The elongated member is configured to move the body between an extended position and a retracted position, such that in the retracted position, the elongated member is received within the inner diameter of the receiving member such that the protrusion is spaced apart from the flange. In the extended position, the elongated member is extended away from the first end of the receiving member such that the second end of the receiving member and the first terminating end of the elongated member are adjacent and the protrusion abuts the flange such that the distance between the pair of lobes is increased.

In another aspect, an occlusion device configured to cause embolization of a blood vessel is provided. The occlusion device includes a body, a pair of lobes, and an adjustment assembly. The body includes a distal portion and a proximal portion. One of the pair of lobes is positioned at the distal portion. One of the pair of lobes is positioned at the distal portion of the body and the other one of the pair of lobes is positioned at the proximal portion of the body. Each lobe of the pair of lobes is shaped to circumferentially contact a vessel wall of the blood vessel to occlude the blood vessel. The body includes an adjustment assembly positioned between the distal portion and the proximal portion to change a distance between the pair of lobes. The adjustment assembly includes a receiving member and an elongated member. The receiving member has a first end, a second end and an inner diameter. The second end has a flange that extends radially inward into the inner diameter. The elongated member has a first terminating end, a second terminating end and an outer diameter. The first terminating end having a protrusion that extends radially outward from the outer diameter. The elongated member is configured to move the body between an extended position and a retracted position, such that in the retracted position, the elongated member is received within the inner diameter of the receiving member such that the protrusion is spaced apart from the flange. In the extended position, the elongated member is extended away from the first end of the receiving member such that the second end of the receiving member and the first terminating end of the elongated member are adjacent and the protrusion abuts the flange such that the distance between the pair of lobes is increased.

In another aspect, a method for embolization of a blood vessel is provided. The method includes inserting, by a delivery device, an occlusion device into the blood vessel, the occlusion device having a body and a pair of lobes, the body has a distal portion and a proximal portion, one of the pair of lobes is positioned at the distal portion of the body and the other one of the pair of lobes is positioned at the proximal portion of the body, positioning the occlusion device at a target location and deploying one of the pair of lobes within the blood vessel such that the one of the pair of lobes circumferentially contact a diameter of the blood vessel to provide a radial force for stability at the target location. The method continues by adjusting a distance between the pair of lobes of the occlusion device via an adjustment assembly such that the pair of lobes are positioned on either side of the target location and deploying the other one of the pair of lobes within the blood vessel such that the pair of lobes circumferentially contact the diameter of the blood vessel to inhibit a blood flow at the target location and to provide the radial force for stability at the target location.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein generally relate to vascular occlusion devices that include a body that may be adjustable, connecting a pair of lobes for embolization of peripheral vasculature, for example though other vessels are contemplated and possible. The pair of lobes may be a self-expanding metallic mesh, Nitinol fibers segments, or the like. The pair of lobes may inhibit fluid flow, such as a blood flow, and may expand to match the diameter of the vessel, providing sufficient radial force for stability at a target location. In embodiments, each of the pair of lobes may be generally cylindrical in shape with closed ends to allow recapture of the device after deployment. The body includes various adjustable devices that allow the body to move between an extended position and a retracted position. The retracted position is the minimum space between the pair of lobes. The extended position is a largest gap, or space, between the pair of lobes. As such, the body increases a length of the occlusion device to a desired length. Further, in some embodiments the body may only be moved between the retracted and the extended position when a proximal lobe of the pair of lobes is still within the delivery system, thereby allowing adjustment prior to full deployment. Moreover, in some embodiments, the pair of lobes may be recaptured if the location or length is not optimal. Additionally, in some embodiments the body may further include a radiopaque material to allow easy visualization of the occlusion device length under fluoroscopy.

As such, the embodiments described herein produce desirable results over existing solutions, such as providing a user with the freedom to adjust the device on demand to tailor the device to the anatomy of the patient.

Various embodiments of vascular occlusion devices and methods of use thereof are described in detail herein.

Figures 1, 2:
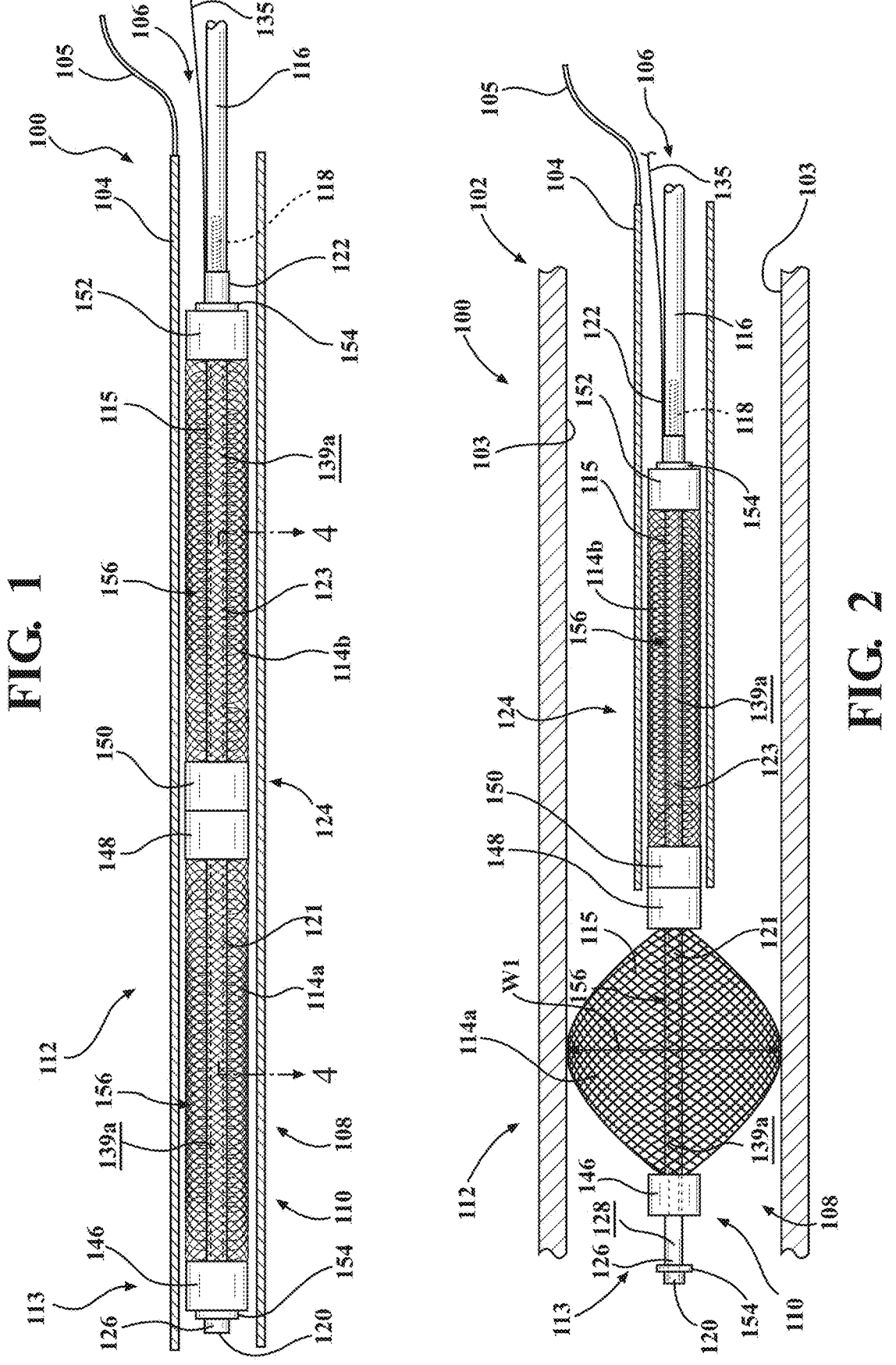
FIG. 1 schematically depicts a vascular occlusion device with a pair of lobes in a low profile configuration, according to one or more embodiments shown and described herein.
FIG. 2 schematically depicts the vascular occlusion device of FIG. 1 with one of the pair of lobes in a low profile configuration and the other lobe of the pair of lobes in a deployed configuration, according to one or more embodiments shown and described herein.
Figure 3:
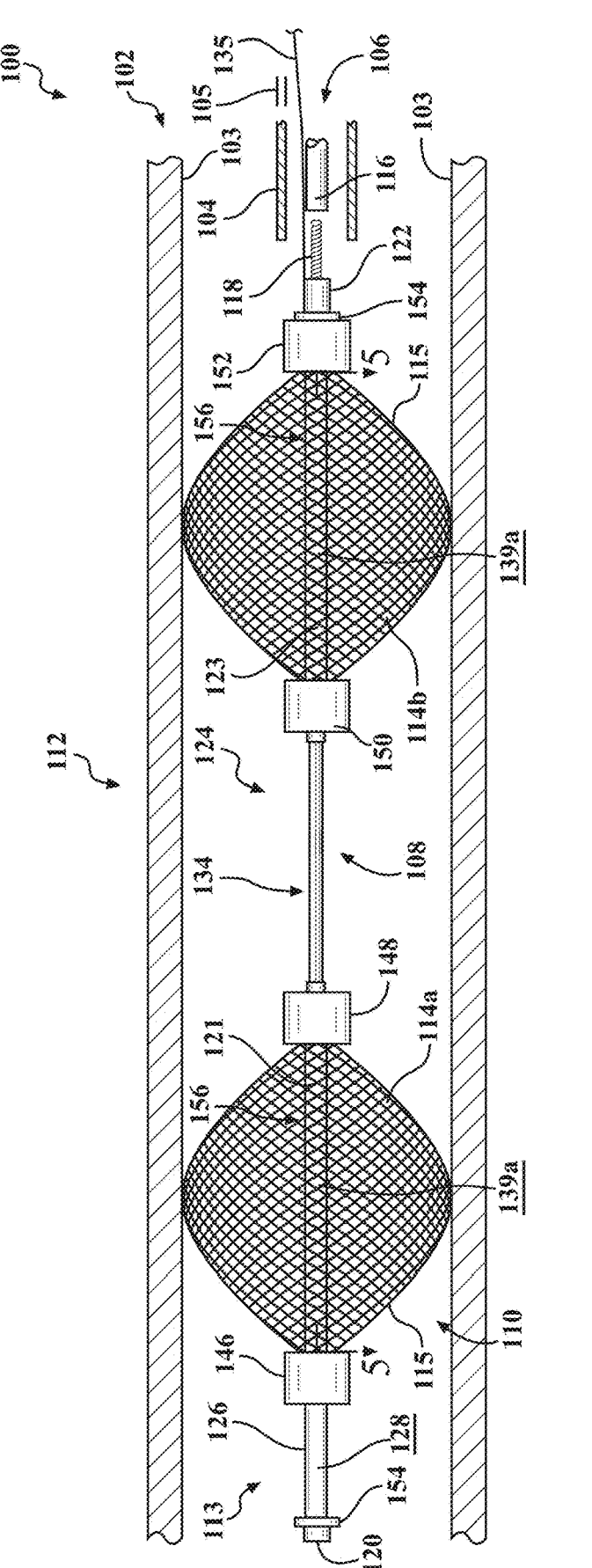
FIG. 3 schematically depicts the vascular occlusion device of FIG. 1 with the pair of lobes in the deployed configuration, according to one or more embodiments shown and described herein.

Referring initially to FIGS. 1-3, a first embodiment of a vascular occlusion system 100 for occluding a blood vessel 102 is schematically depicted. For example, the blood vessel 102 may include any artery, vein, capillary, or the like. Further, the blood vessel 102 includes a wall 103 that maintains a fluid, such as blood, therein. The vascular occlusion system 100 may generally include a sheath 104, a tether 105, a delivery assembly 106 and a vascular occlusion device 108. The vascular occlusion device 108 generally includes a body 110 extending between and beyond a pair of lobes 112, which are spaced apart. The vascular occlusion device 108 may further include a plurality of radiopaque markers 113. One of the pair of lobes 112 is a distal lobe 114*a* and the other is a proximal lobe 114*b* with respect to the delivery assembly 106.

FIG. 1 schematically depicts the vascular occlusion device 108 in an unexpanded state as it is delivered to a desired occlusion position or target within the blood vessel 102 via the delivery assembly 106. As shown in FIG. 1, the delivery assembly 106 generally includes a delivery catheter 116, which may act as a guidewire that may be releasably coupled to the body 110 of the vascular occlusion device 108 via an attachment device 118. As illustrated, the attachment device 118 may be part of the delivery catheter 116. However, this is non-limiting and the attachment device 118 may be a separate component from the delivery catheter 116. The delivery catheter 116 may extend from the vascular occlusion device 108 and outside of the target area to control the delivery assembly 106. The delivery catheter 116 may be various materials, such as latex, silicone. Teflon, PEEK, polyethylene terephthalate, high-density polyethylene, polyvinyl chloride, low-density polyethylene, polypropylene, polystyrene, copper, aluminum, stainless steel, surgical grade steel, combinations thereof, and/or the like.

Further, the vascular occlusion system 100 includes the sheath 104, which may be slidably removable from the vascular occlusion device 108. The sheath 104 may be a liner that maintains a shape of the pair of lobes 112 during delivery of the vascular occlusion device 108 into the target area, as discussed in greater detail herein. The sheath 104 may comprise a variety of materials, such as, without limitation, latex, silicone, Teflon, PEEK, polyethylene terephthalate, high-density polyethylene, polyvinyl chloride, low-density polyethylene, polypropylene, polystyrene, polyesters, Polyether block amid, Polydimethylsiloxane, copper, aluminum, stainless steel, surgical grade steel, combinations thereof, and/or the like.

The tether 105 may be a guide wire, string, and/or the like, and may be coupled or attached to the sheath 104 such that movement of the tether 105 may remove the sheath 104 from the vascular occlusion device 108. That is, the sheath 104 is removed by the tether 105 by a movement of the tether 105 in a direction opposite of an insertion direction of the vascular occlusion device 108. In some embodiments, the tether 105 may be coupled to the sheath 104 via a hook and loop engagement. In other embodiments, the tether 105 may be coupled to the sheath 104 via traditional joining methods such as plastic welding, adhesives, epoxy, a fastener such as a bolt and nut, rivet, screw, and/or the like. The tether 105 may be various materials, such as, latex, silicone, Teflon, PEEK, polyethylene terephthalate, high-density polyethylene, polyvinyl chloride, low-density polyethylene, polypropylene, polystyrene, polyesters, Polyether block amid, Polydimethylsiloxane, copper, aluminum, stainless steel, surgical grade steel, combinations thereof, and/or the like.

In embodiments, the vascular occlusion device 108 may be delivered by the delivery assembly 106 into the blood vessel 102 with the sheath 104 lining or covering the vascular occlusion device 108, thereby holding the occlusion device 108 in a low-profile delivery configuration. Each of the pair of lobes 112 move between a low profile configuration, as best illustrated in FIG. 1, to a deployed configuration, as best illustrated in FIG. 3. As discussed in greater detail herein, in the low profile configuration, fluid in the blood vessel 102 may pass by the vascular occlusion device 108 and in the deployed configuration, each of the pair of lobes 112 radially expand to occlude or substantially occlude the fluid flow within the blood vessel 102 from flowing or passing through the vascular occlusion device 108.

The sheath 104 holds or maintains the pair of lobes 112 in the low profile configuration, as discussed in greater detail herein. That is, in the low profile configuration, at least one of the pair of lobes 112 is compressed into the depicted low profile configuration and is positioned within the sheath 104 such that the sheath 104 holds or maintains each of the pair of lobes in the low profile configuration, as best seen in FIG. 1.

It is noted that while the vascular occlusion device 108 is illustrated in the unexpanded state where the pair of lobes 112 are in the low profile configuration to allow delivery of the vascular occlusion device 108 into the blood vessel 102, this is non-limiting and each of the pair of lobes 112 of the vascular occlusion device 108 may transition from the low profile configuration to the deployed configuration as the vascular occlusion device 108 is being delivered by the delivery assembly 106 to the blood vessel 102. Accordingly, the pair of lobes 112 of the vascular occlusion device 108 may begin expanding when desired by the user.

Still referring to FIGS. 1-3, each of the pair of lobes 112 of the vascular occlusion device 108 generally includes a shape memory portion formed of a suitable shape memory material (e.g., Nitinol® or a suitable shape memory polymer such as some polyurethanes and polyethylene terephthalate) such that the pair of lobes 112 may each be self-expandable, self-moveable, or transition, between the low profile configuration and the deployed configuration. That is, in one embodiment, each of the pair of lobes 112 may comprise a self-expanding mesh 115 that is the shape memory portion.

As such, when the compression caused from the sheath 104 is removed from each of the pair of lobes 112, the self-expanding mesh 115 of each of the pair of lobes 112 may self-expand into the deployed configuration. The pair of lobes 112 may inhibit fluid flow and may expand to match the diameter of the wall 103 of the blood vessel 102, providing sufficient radial force for stability at a target location. In embodiments, each of the pair of lobes 112 may be cylindrical in shape with closed ends. In other embodiments, each of the pair of lobes 112 may be square, rectangular, hexagonal, octagonal, in shape with closed ends, and/or the like. Further, the closed ends each of the pair of lobes 112 may allow recapture of the vascular occlusion device 108 after deployment into the blood vessel 102 via a guidewire, catheter, and/or other known retrieval tools.

In other embodiments, each of the pair of lobes 112 may not be self-expanding, but may be expanded via a fluid pump (e.g., the pair of lobes 112 may be balloons fluidly connected to one or more inflation catheters configured to deliver fluid to the interior of the balloons), or via another mechanical device operated by a user.

The self-expanding mesh 115 may include a plurality of segments or individual wires overlapping with one another so to provide the flexibility of a mesh, but the openings of the pores of the mesh together have diameters that are smaller than the blood molecules in blood or other fluids, such as blood, to freely and/or easily pass through. As such, the pair of lobes, in the deployed configuration, substantially occlude blood flow through the blood vessel 102. The deployed configuration may be limited by a diameter of the wall 103 of the blood vessel 102, as discussed in greater detail herein. As such, each of the pair of lobes 112 may extend in the deployed configured to match the diameter of the wall 103 of the blood vessel 102, and become anchored thereto. Moreover, the self-expanding mesh 115 of each of the pair of lobes 112 may expand to different sizes (i.e. a first of the lobes 112 may be configured to expand to a first size having a first radial extent, and a second of the lobes 112 may be configured to expand to a second size having a second radial extent which is different to the first radial extent) to accommodate various target areas within the blood vessel 102, such as, for example, where a shape of the blood vessel 102 may be conical shaped.

The body 110 may be a stem or an elongated member, which includes a distal end 120 and an opposite proximal end 122. In some embodiments, the stem or the elongated member may include a rod 126, which may extend between the proximal end 122 and the distal end 120 to define a length of the body 110. Moreover, the body 110 may include a distal portion 121 and a proximal portion 123, each positioned near the respective distal end 120 and proximal end 122. The distal end 120 may be distal of the distal lobe 114*a* and the proximal end 122 may be positioned between the proximal lobe 114*b* and the delivery assembly 106. As such, the delivery catheter 116 of the delivery assembly 106 may be in contact with the proximal end 122 when the delivery assembly 106 is in contact with the body 110 of the vascular occlusion device 108. In some embodiments, the rod 126 may be rigid. In other embodiments, the rod 126 may be flexible. The rod 126 may comprise different materials, such as, without limitation, vinyl, polyvinyl chloride, latex, rubber, silicone, combinations thereof, or other suitable materials. Further, in some embodiments, the rod 126 or portions thereof may be solid (non-hollow). In other embodiments, the rod 126 or portions thereof may be hollow with a lumen, such as those found in catheters. As such, the rod 126 or portions thereof may be flexible and/or the rod 126 or portions thereof may be rigid. As such, portions of the body 110 may be solid and rigid while other portions may be hollow and more flexible than the solid portions. For example, the distal portion 121 and/or the proximal portion 123 may be hollow and the proximal end 122 and/or the distal end 120 may be solid, as discussed in greater detail herein.

Still referring to FIGS. 1-3, in some embodiments, the distal lobe 114a may be positioned at the distal portion 121 of the rod 126 and the proximal lobe 114b may be positioned at the proximal portion 123 of the rod 126. As such, portions of the distal lobe 114a may make contact with, and/or slidably engage on the distal portion 121 of the rod 126 and portions of the proximal lobe 114b may make contact with, and/or slidably engage on the proximal portion 123 of the rod 126. In other embodiments, portions of the distal lobe 114a may be fixedly coupled to the rod 126 at the distal portion 121 and portions of the proximal lobe 114b may be fixedly coupled to the rod 126 at the proximal portion 123. The distal lobe 114a and the proximal lobe 114b may be fixedly coupled to the rod 126 at the distal portion 121 and at the proximal portion 123, respectively, via any conventional joining technique (e.g., brazing, welding, adhesives, or the like).

Further, in some embodiments, the distal end 120, the distal portion 121, the proximal portion 123, and the proximal end 122 are cylindrical in shape to define a diameter along the length of the rod 126. For example, the rod 126 may be cylindrical such that the rod 126 defines an outer surface 128. This is non-limiting and the rod 126 may instead be rectangular, octagonal, hexagonal, and/or the like, in shape.

In some embodiments, portion of the body 110 such as the distal portion 121 and/or the proximal portion 123, may each or together have differential cross-section shapes other than cylindrical, for example, rectangular, hexagonal, octagonal, and/or the like. Further, in some embodiments, portions of the body 110, such as the distal portion 121 and/or the proximal portion 123 may each or together have a uniform shape between the proximal and distal ends 120, 122, In other embodiments, the distal portion 121 and/or the proximal portion 123 of the body 110 may each or together have non-uniform or have irregular portions between the distal and proximal ends 120, 122. It should be appreciated that the rod 126 extends through at least portions of the pair of lobes 112.

In some embodiments, the portions of the pair of lobes 112 that are coupled or attached to the body 110, as discussed above, may be attached or coupled to the outer surface 128 of the rod 126. Portions of the pair of lobes 112 that are coupled or attached to the outer surface 128 of the rod 126 may be via any conventional joining technique (e.g., brazing, welding, adhesives, or the like).

Figures 4, 5:
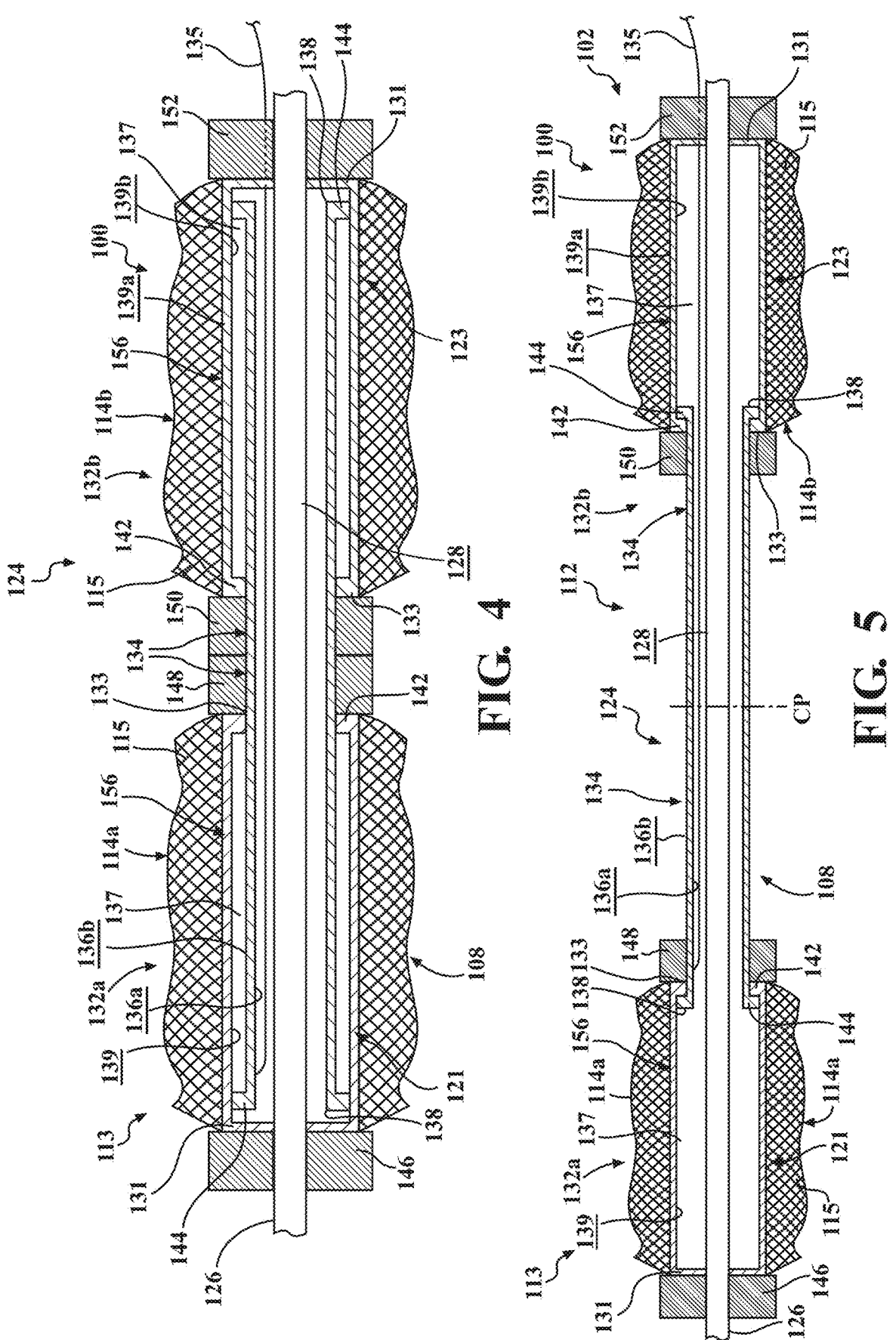
FIG. 4 schematically depicts an isolated cross sectional view of an adjustment assembly of the vascular occlusion device of FIG. 1 taken from line 4-4 in a retracted position, according to one or more embodiments shown and described herein.
FIG. 5 schematically depicts an isolated cross sectional view of the adjustment assembly of the vascular occlusion device of FIG. 3 taken from line 5-5 in an extended position, according to one or more embodiments shown and described herein.

Still referring to FIGS. 1-3 and now also referring to FIGS. 4-5, an adjustment assembly 124 may be positioned to extend axially between the pair of lobes 112. The body 110 may comprise the adjustment assembly 124, which may include portions of the distal portion 121 and/or the proximal portion 123 of the body 110 respectively. The adjustment assembly 124 may be configured to change a longitudinal or axial distance between the pair of lobes 112, as discussed in greater detail herein. In some embodiments, the rod 126 travels through portions of the adjustment assembly 124.

The adjustment assembly 124 may further include a pair of adjustment devices 132a, 132b. The pair of adjustment devices 132a, 132b are positioned to be housed within the distal portion 121 and/or the proximal portion 123 of the body 110 respectively. As such, the pair of adjustment devices 132a, 132b may only extend a total length of the distal portion 121 and/or the proximal portion 123 that houses the pair of adjustment devices 132a, 132b. The total length of the distal portion 121 and/or the proximal portion 123 may be dependent on a length of the lobe 114a, 114b as determined when the lobe 114a, 114b is in the deployed configuration, respectively. As such, while the body 110 may comprise the adjustment assembly 124, the adjustment assembly 124 may not be the entire body 110 and the pair of adjustment devices 132a, 132b may not extend the entire length of the body 110.

Each of the pair of adjustment devices 132a, 132b may be mirror images of each other. As such, only the adjustment device 132a will be discussed in detail herein. In embodiments, the adjustment device 132a may include a receiving member 156 and an elongated member 134. In some embodiments, the receiving member 156 may extend into and be part of and/or form the distal portion 121 and the proximal portion 123, respectively. The receiving member 156 may include an outer surface 139a and an opposite inner surface 139b.

Portions of the receiving member 156 may be in contact with the mesh 115 at the distal portion 121. For example, the outer surface 139a of the receiving member 156 may be in contact with the mesh 115. In some embodiments, the distal lobe 114a may be fixedly coupled to the outer surface 139a of the receiving member 156 of the adjustment device 132a. As such, it should be understood that the adjustment device 132a, and components thereof (e.g., the receiving member 156 and the elongated member 134) may be a part of the body 110. In other embodiments, the distal lobe 114a may be positioned at the receiving member 156 of the adjustment device 132a. As such, portions of the distal lobe 114a may make contact with, and/or slidably engage on the receiving member 156 of the adjustment device 132a.

Now referring to FIGS. 4-5, the receiving member 156 may include a first end 131 and an opposite second end 133. The second end 133 is open such that the first end 131 and the inner surface 139b of the receiving member 156 form a cavity 137, or lumen, within the receiving member 156. The second end 133 may include a flange 142 that extends radially inward from the inner surface 139b into the cavity 137.

The elongated member 134 has an inner surface 136a and an opposite outer surface 136b with an outer diameter that is less that a diameter of the cavity 137. The elongated member 134 may further include a pair of terminating ends 138 positioned at opposite ends of the elongated member 134. Both of the pair of terminating ends 138 may be open ended and each of the pair of terminating ends 138 may further include a protrusion 144. The protrusion 144 may extend radially outward from the outer surface 136b of the elongated member 134 and within the cavity 137 of the receiving member 156.

As such, the cavity 137 receives the elongated member 134 as illustrated best in FIG. 4. The elongated member 134 may be configured to slidably move within the cavity 137 between an extended position, as best illustrated in FIG. 5, and a retracted position, as best illustrated in FIG. 4 via the guidewire 135 (e.g., for the adjustment device 132a) and/or the delivery catheter 116 of the delivery assembly 106 (e.g., for the adjustment device 132b), as discussed in greater detail herein. In other embodiments, it should be understood that there may be more than one elongated member that slidably moves within the cavity 137 and each of the elongated members may be telescoped within each other.

In the retracted position, the elongated member 134 may be slide within the cavity 137 of the receiving member 156 such that the protrusion 144 is axially spaced apart from the flange 142 by the length of the portion of the elongated member 134 which is within the cavity 137. In the extended position, the elongated member 134 may be slide axially toward the second end 133 and within the cavity 137 such that the terminating ends 138 and the protrusion 144 are axially moved closer to the flange 142 until the protrusion 144 abuts the flange 142 such that the distance between a center point CP of the elongated member 134 and a distal portion of the distal lobe 114*a* is increased by the half length of the elongated member 134. It should be understood that the elongated member 134 may be configured to slidably move to a plurality of positions within the cavity 137 between the extended position and the retracted position and is only limited by the length of the elongated member 134 and the positioning of the protrusion 144 and/or the flange 142. As such, it should be understood that the guidewire 135 may be used to move the elongated member 134 of the adjustment device 132*a* between the plurality of positions, with respect to the receiving member 156, once the distal lobe 114*a* is in the deployed position, as discussed in greater detail herein.

Further, the delivery catheter 116 of the delivery assembly 106 may be used in conjunction with the guidewire 135 or separately from the guidewire 135, to move the elongated member 134 of the adjustment device 132*b* between the plurality of positions, with respect to the receiving member 156, once the elongated member 134 of the adjustment device 132*a* is set, as discussed in greater detail herein. As such, the extension of the body 110 of the vascular occlusion device 108 may be temporary, repositionable or may be adjustable an infinite number of times.

That is, the guidewire 135 may be used to position or move the elongated member 134 for the adjustment device 132*a* within the cavity 137 and between the plurality of positions between the extended position and the retracted position. To lock the position of the elongated member 134 for the adjustment device 132*a*, the guidewire 135 may be pinned or otherwise inhibited from movement. As such, with the guidewire 135 immobilized, the elongated member 134 may be locked into position and inhibited from further movement. It should be understood that the pinning or inhibiting of movement of the guidewire 135 may be completed exterior to the body 110 of the vascular occlusion device 108. On the other hand, the delivery catheter 116 of the delivery assembly 106 may be used to move the elongated member 134 of the adjustment device 132*b* between the plurality of positions.

The elongated member 134 of the pair of adjustment devices 132*a*, 132*b* may extend and retract in a direction towards one another such that, in the fully expanded position, the adjustment assembly 124 may be increased in length by 100 percent, for example. In some embodiments, the increase in length may be in a co-axial direction. In other embodiments, the increase in length and/or may be offset with respect to the adjustment devices 132*a*, 132*b*. For example, each of the pair of adjustment devices 132*a*, 132*b* may extend axially but offset from one another when the vascular occlusion device 108 is positioned within a curvilinear portion of the blood vessel 102. That is, each of the pair of adjustment devices 132*a*, 132*b* may not share a common axis.

Each of the pair of adjustment devices 132*a*, 132*b* are independently adjustable to a desired length. That is, the adjustment device 132*a* may be fully extended (e.g., 50 percent of a total adjustable length of the body 110) and the adjustment device 132*b* may only be adjusted to a desired position that is less than the extended position. It should be appreciated that this is non-limiting and that the adjustment device 132*a* may be partially adjusted in length while adjustment device 132*b* remains in the retracted position, in the fully extended position, and/or the like. As such, the independently adjustable pair of adjustment devices 132*a*, 132*b* provides the user with flexibility in reaching and occluding a target area of the blood vessel 102. When the increased length of the body 110 is no longer required, in some embodiments, the adjustment devices 132*a*, 132*b* may be retracted. As such, the extension of the body 110 of the vascular occlusion device 108 may be temporary and/or repositionable between the extended position and the retracted position. That is, the in one embodiment, the pinning or inhibiting the guidewire 135 from further movement may be reversed such that the delivery assembly 106 may be used to move or reposition a length of the body 110. Further, the tether 105 and sheath 104 may be repositioned to move the pair of lobes 112 from the deployed position back into the retracted position, as discussed in greater detail herein.

In some embodiments, extension of the adjustment devices 132*a*, 132*b* may be permanent or locked until unlocked. For example, the elongated member 134 may include at least one resilient protrusion extending radially outward from the outer surface 136*b* and that may ride along the inner surface 139*b* of the cavity 137. The at least one resilient protrusion may be received within a corresponding at least one notch of the cavity 137. Each of the corresponding at least one notches of the cavity 137 may be positioned at the cavity stop end 133 (e.g., the fully extended position) such that the elongated member 134 may be locked into the extended position when the at least one resilient protrusion is received by the corresponding at least one notch of the cavity 137. In such embodiments, the extension of the body 110 of the vascular occlusion device 108 may be permanent. That is, the extension of the body 110 of the vascular occlusion device 108 may not be reversible.

The plurality of radiopaque markers 113 may be coupled or attached the outer surface 128 of the rod 126. In a non-limiting example, as illustrated the plurality of radiopaque markers 113 includes a first marker 146 positioned between the distal end 120 and the distal lobe 114*a* and may be in contact with the distal lobe 114*a*. A second marker 148 may be positioned on an opposite side and in contact with the distal lobe 114*a* opposite the contact with the first marker 146. A third marker 150 may be positioned between the pair of lobes 112, abutting the second marker 148, and may be in contact with the proximal lobe 114*b*. A fourth marker 152 may be positioned between the proximal end 122 and the proximal lobe 114*b* and may be in contact with the proximal lobe 114*b* opposite the contact with the third marker 150.

In some embodiments, each of the plurality of radiopaque markers 113 may be a band that extends around a circumference of the outer surface 128 of the rod 126. In other embodiments, each of the plurality of radiopaque markers 113 may be an annular ring that extends around a circumference of the outer surface 128 of the rod 126. Further yet, in other embodiments, the plurality of radiopaque markers 113 may be a combination of bands and/or annular rings, and/or may be other shapes or combinations, such as, for example, a conical shape, an elliptical shape, a square shape, a triangular shape, and/or the like.

In some embodiments, the plurality of radiopaque markers 113 may be coupled or attached to the outer surface 128 of the rod 126 via traditional methods, such as by epoxy, adhesive, fasteners such as set screws, bolt and nuts, and/or the like. As such, in these embodiments, some or all of the plurality of radiopaque markers 113 may be stationary or fixedly coupled into position.

In some embodiments, at least one of the plurality of radiopaque markers 113 may be slidably engaged with the outer surface 128 of the rod 126. For example as illustrated in FIGS. 2-3, when the distal lobe 114a is moved from the low profile configuration into the deployed configuration, the first marker 146 may slidably move in a direction away from the distal end 120 with the distal lobe 114a expansion. That is, in the low profile configuration, a distance between the first marker 146 and the distal end 120 may be less than the distance between the first marker 146 and the distal end 120 when the distal lobe 114a is in the deployed configuration. As such, the first marker 146 may be able to accurately mark the terminating end of the distal lobe 114a when the distal lobe is in both the low profile configuration and the deployed configuration.

Each of the radiopaque markers 113 may comprise a radiopaque material such as tungsten-filled polymers, such as nylons, pebax, and polyurethanes, thermoplastic elastomers, barium sulfate, bismuth compounds, and/or the like.

Further, it should be appreciated each length of the elongated member 134 on either side of the center point CP may be similar lengths such that the elongated member 134 fits within the cavity 137 and between at least two of the plurality of radiopaque markers 113, as discussed in greater detail herein. As such, the plurality of radiopaque markers 113 may be strategically positioned along the outer surface 128 of the rod 126 to show the user the positioning of certain features of the body 110 such as the current position of the elongated member 134 within the cavity 137 somewhere between the extended position and the retracted position.

A pair of stopper plates 154 may be positioned respectively at the distal and proximal ends 120, 122 of the rod 126. It should be appreciated that the pair of stopper plates 154 may prevent the first and fourth markers 146, 152 from moving towards the distal end 120 and/or proximal end 122 and/or from moving off the rod 126 during insertion and removal of the vascular occlusion device 108. In some embodiments, the pair of stopper plates 154 are monolithically formed with the rod 126. In other embodiments, the pair of stopper plates 154 are coupled to the outer surface 128. For example, in some embodiments, each of the pair of stopper plates 154 may be coupled to the rod 126 via a fastener such as a setscrew, hook and loop fastener, adhesive, epoxy, weld, and/or the like. In other embodiments, each of the pair of stopper plates 154 are coupled to the rod 126 via a snap fit connection. In some embodiments, each of the pair of stopper plates 154 may have a diameter less than the first and fourth markers 146, 152. In other embodiments, each of the pair of stopper plates 154 may have a diameter equal to or greater than the first and fourth markers 146, 152.

Now referring back to FIG. 2, which schematically depicts the distal lobe 114a in the deployed configuration. The sheath 104 is removed from the distal lobe 114a permitting the distal lobe 114a to move from the low profile configuration into the deployed configuration. As such, the distal lobe 114a self-expands to be in radial contact with the blood vessel 102 via the shape memory effect. For example, when fabricated, the pair of lobes 112 of the vascular occlusion device 108 may be manipulated in shape to comprise a diameter or circumference W1 that is greater than or equal to a diameter of the wall 103 of the blood vessel 102, if allowed to expand unimpeded. When in the blood vessel 102, the distal lobe 114a of the vascular occlusion device 108 may expand until stopped by the wall 103 of the blood vessel 102. As a result of the mechanical impedance from the wall 103, the self-expanding mesh 115 of the distal lobe 114a may apply a radial force against the wall 103. The radial force supplied by the self-expanding mesh 115 may anchor portions of the distal lobe 114a into the wall 103, thereby securing the vascular occlusion device 108 at a desired occlusion position. While the distal lobe 114a is depicted as including the self-expanding mesh 115, it should be appreciated that the mesh may be a plurality of radially-extending segments that are linear, may be bent or curved (e.g., as a result of compression from encountering the wall 103) in any shape in accordance with the present disclosure. Embodiments are also envisioned where the self-expanding mesh 115 does not extend in straight lines by design (e.g., some of the mesh that forms the self-expanding mesh 115 may include sub-segments that extend in different directions from one another) to facilitate occluding fluid flow.

Referring collectively to FIGS. 2, and 4-5, once the distal lobe 114a is in the deployed configuration, the length of the body 110 may be adjusted via the adjustment devices 132a, 132b. That is, with portions of the distal lobe 114a secured into the wall 103 of the blood vessel 102, the elongated member 134 may be extended between the plurality of positions to set a length of the body 110 to a desired length prior to the removal of the sheath 104 and the expansion of the proximal lobe 114b. When the desired length of the body 110 is achieved, the sheath 104 is removed from the proximal lobe 114b, thereby causing the proximal lobe 114b to move from the low profile configuration into the deployed configuration and anchoring the vascular occlusion device 108 at a desired occlusion position.

That is, with reference to FIG. 3, the proximal lobe 114b is depicted in the deployed configuration. As such, the proximal lobe 114b self-expands to be in radial contact with the wall 103 of the blood vessel 102 via the shape memory effect. When in the blood vessel 102, the proximal lobe 114b of the vascular occlusion device 108 may expand until stopped by the wall 103 of the blood vessel 102. As a result of the mechanical impedance from the wall 103, the self-expanding mesh 115 of the proximal lobe 114b may apply a radial force against the wall 103. The radial force supplied by the self-expanding mesh 115 may anchor portions of the proximal lobe 114b into the wall 103, thereby securing the vascular occlusion device 108 at a desired occlusion position. While the proximal lobe 114b is depicted as including self-expanding mesh 115, it should be appreciated that the self-expanding mesh 115 may be a plurality of radially-extending segments that are linear, may be bent or curved (e.g., as a result of compression from encountering the wall 103) in any shape in accordance with the present disclosure. Embodiments are also envisioned where the self-expanding mesh 115 does not extend in straight lines by design (e.g., some of the mesh that forms the self-expanding mesh 115 may include sub-segments that extend in different directions from one another) to facilitate occluding fluid flow.

Referring to FIGS. 1-5, while the vascular occlusion device 108 is depicted to only include the pair of lobes 112 and the adjustment assembly 124, any number of lobes and/or additional adjustment assemblies may be included consistent with the present disclosure. In embodiments, for example, the vascular occlusion device 108 includes two pair of lobes and two adjustment assemblies positioned between each of the pair of lobes. A greater number of lobes may also aid in occluding fluid flow within the blood vessel 102, as the lobes may extend in different directions within the blood vessel (e.g., at different azimuthal orientations relative to the depicted radial direction). Increasing the number of lobes may increase the portion of the blood vessel 102 that is directly blocked by the vascular occlusion device 108, thereby providing more complete occlusion of fluid flow.

Figure 6:
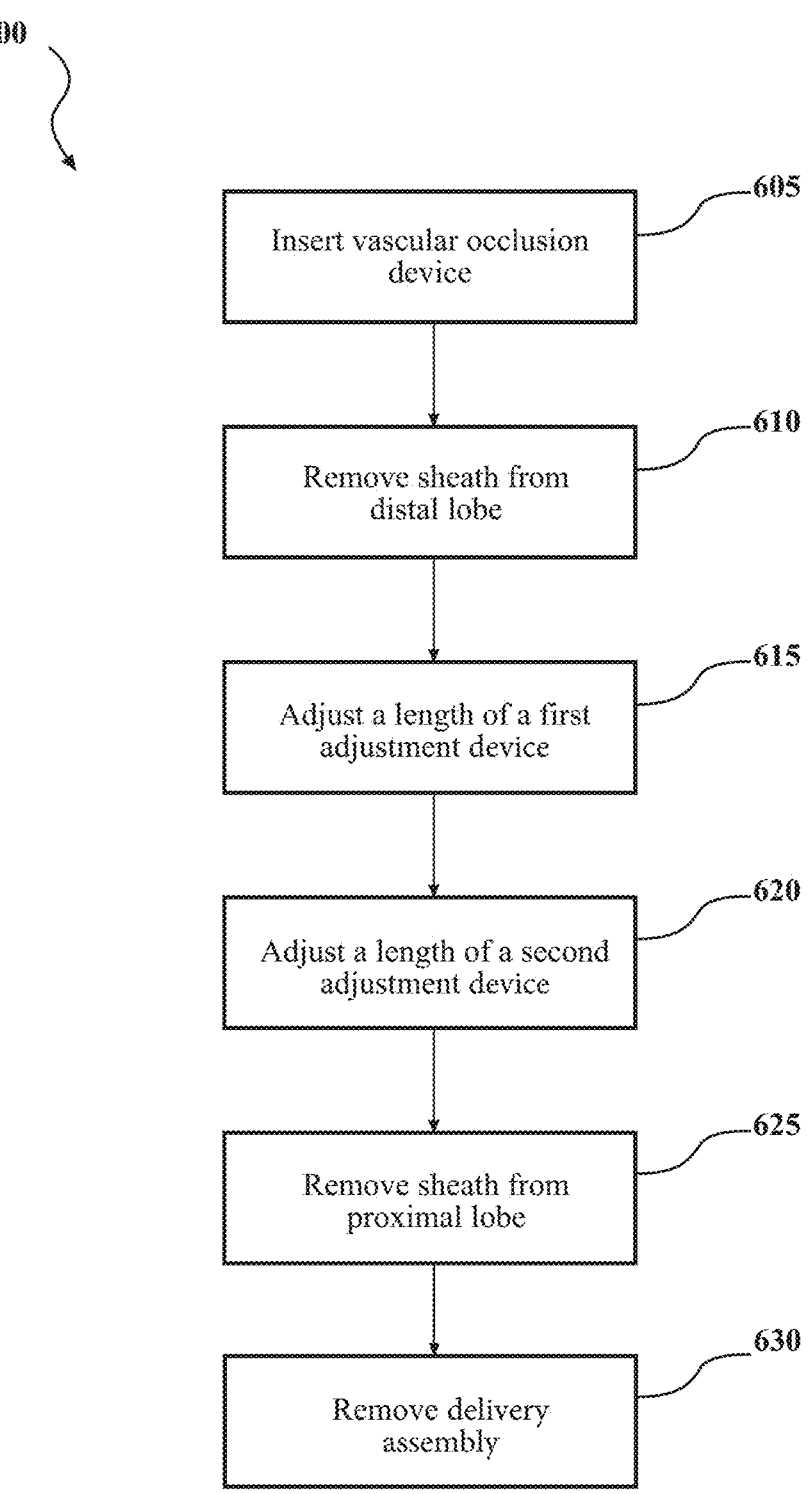
FIG. 6 depicts a flow diagram of an illustrative method of placing the vascular occlusion device of FIG. 1 according to one or more embodiments shown and described herein FIG. 7 schematically depicts a second aspect of a vascular occlusion device with a pair of lobes in a low profile configuration, according to one or more embodiments shown and described herein.

Referring now to FIG. 6, a flow diagram that graphically depicts an illustrative method 600 of placing the vascular occlusion device 108 is provided. Although the steps associated with the blocks of FIG. 6 will be described as being separate tasks, in other embodiments, the blocks may be combined or omitted. Further, while the steps associated with the blocks of FIG. 6 will described as being performed in a particular order, in other embodiments, the steps may be performed in a different order. The method 600 may also be used to place the vascular devices 208, 308 or 408 disclosed herein.

At block 605, the vascular occlusion device 108 is inserted or advanced into the blood vessel 102 and moved to a desired target area. In some embodiments, the target area may be anywhere that includes a length or portion of the vessel for which the occlusion is desired. At block 610, the sheath may be removed from the distal lobe 114*a* via the tether 105, or guide wire, such that the distal lobe 114*a* moves from the low profile configuration to the deployed configuration. Once in the deployed configuration, the length of the body 110 may be adjusted via the adjustment device 132*a*, at block 615 and via the adjustment device 132*b*, at block 620. That is, once portions of the mesh 115 of the distal lobe 114*a* is secured into the wall 103 of the blood vessel 102, there may be sufficient radial force for stability at the target location such that the vascular occlusion device 108 is anchored in position. The elongated member 134 may be extended between the plurality of positions to set a length of the body 110 to a desired length prior to the removal of the sheath 104 and the expansion of the proximal lobe 114*b*. When the desired length of the body 110 is achieved, the sheath 104 is removed causing the proximal lobe 114*b* to move from the low profile configuration into the deployed configuration, thereby anchoring the vascular occlusion device 108 at a desired occlusion position, at block 625. At block 630, the delivery assembly 106 is removed. In some embodiments, the removing of delivery assembly 106 may be via twisting to remove the delivery catheter 116, rotating to unthread the delivery catheter 116, and/or the like.

As such, it should be appreciated that the pair of lobes 112 in the deployed position are a pair of lobes that occlude a fluid from passing into the target area, between the distal lobe 114*a* and the proximal lobe 114*b*. That is, the pair of lobes 112, in the deployed configuration, inhibit a fluid flow through the blood vessel. Further, it should be appreciated that body 110 may be extended to a plurality of positions between the extended position and the retracted position. The retracted position may be described as the minimum space between the pair of lobes 112. The extended position may be described as a largest gap, or space, between the pair of lobes 112. As such, the body 110 increases a length of the vascular occlusion device 108 to a desired length.

It should be appreciated that the above blocks may be repeated in reverse order to move and/or remove the vascular occlusion device 108 from the blood vessel 102.

Figures 7, 8, 9:
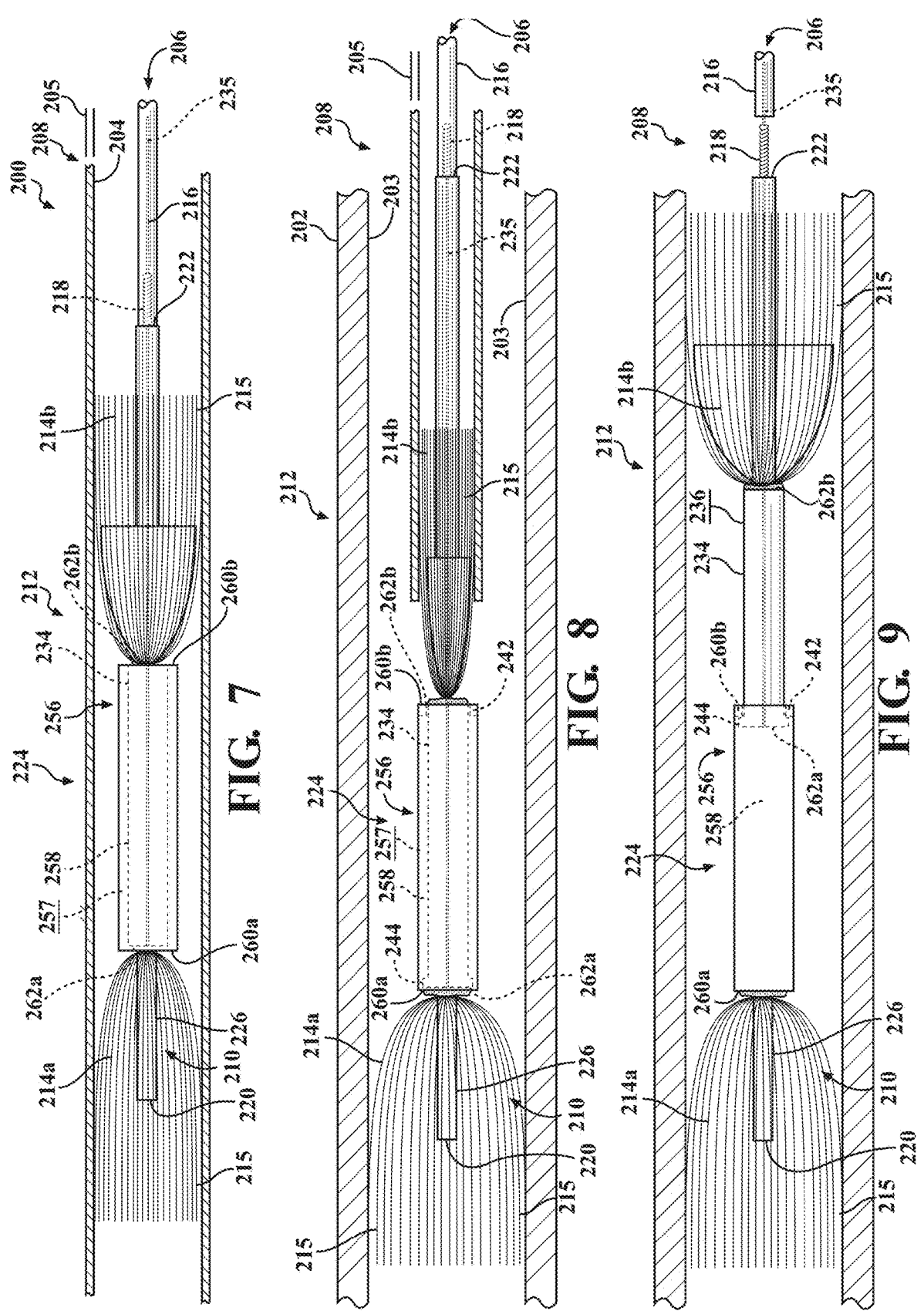
FIG. 8 schematically depicts the vascular occlusion device of FIG. 7 with one of the pair of lobes in a low profile configuration and the other lobe of the pair of lobes in a deployed configuration, according to one or more embodiments shown and described herein.
FIG. 9 schematically depicts the vascular occlusion device of FIG. 8 with both of the pair of lobes in the deployed configuration and the adjustment assembly in an extended position, according to one or more embodiments shown and described herein.

Now referring to FIGS. 7-9, another embodiment of a vascular occlusion device 208 is schematically depicted. It is understood that the vascular occlusion device 208 is similar to the vascular occlusion device 108 with the exceptions of the features described herein. As such, like features will use the same reference numerals with a prefix "2" for the reference numbers. As such, for brevity reasons, these features will not be described again.

The vascular occlusion device 208 includes a body 210 and may be positioned between a pair of lobes 212, which are spaced apart. One of the pair of lobes 212 is a distal lobe 214*a* and the other is a proximal lobe 214*b* with respect to the delivery assembly 206. Each of the pair of lobes 212 move between a low profile configuration, as best illustrated in FIG. 6, to a deployed configuration, as best illustrated in FIG. 8. Each of the pair of lobes 212 of the vascular occlusion device 208 generally includes a shape memory portion formed of a plurality of fibers 215 such that the pair of lobes 212 are each self-expandable, self-movable, or transition, between the low profile configuration and the deployed configuration.

Each of the fibers of the plurality of fibers 215 for each of the pair of lobes 212 may extend from a respective attachment portion of the body 210 such that each of the fibers of the plurality of fibers 215 may overlap with one another. That is, each of the plurality of fibers 215 may radially extend from the body 210 to circumferentially surround a portion of the body 210 and have a length to extend into the blood vessel 202 and between the wall 203 of the blood vessel 202. As such, in some embodiments, each of the pair of lobes 212 may be a conical or frustoconical in shape. In other embodiments, each of the fibers of the plurality of fibers 215 for each of the pair of lobes 214 may extend from anywhere on the body 210 and each of the pair of lobes 212 may be other expanded shapes such as cylindrical, square, rectangular, hexagonal, and/or the like.

In some embodiments, the direction of the opening of each of the pair of lobes 212 in the expanded shape may be opposite of each other. That is, the opening of the conical or frustoconical shape of each of the pair of lobes 212 may open in opposite directions such that the closed ends the opening of the conical or frustoconical shape are adjacent to one another with respect to the respective attachment portion of the body 210.

In embodiments, each of the fibers of the plurality of fibers 215 may have lengths that differ from one another. For example, in some embodiments, some fibers of the plurality of fibers 215 vary from one another in length, but still aid in occluding fluid flow. In some embodiments, less than all of the plurality of fibers 215 contact the wall 103 of the blood vessel 102. A wide variety of combinations of fibers of the plurality of fibers 215 are contemplated and within the scope of the present disclosure.

As such, each of the fibers of the plurality of fibers 215 may provide flexibility within the lobe and may also limit size or diameter of any openings such that a fluid, such as blood, may not freely pass through. That is, the pair of lobes 212 may inhibit fluid flow and may expand to match the diameter of the blood vessel 202, providing sufficient radial force for stability at a target location. As such, the pair of lobes 214, in the deployed configuration, apply occlusion techniques to the blood vessel 202 positioned therein, as discussed in greater detail herein. The deployed configuration may only be limited by a diameter of the blood vessel 202, as discussed in greater detail herein. As such, each of the pair of lobes 212 may extend in the deployed configured to match the diameter of the blood vessel 102. Moreover, the plurality of fibers 215 of each of the pair of lobes 212 may be different sized from one another to accommodate for target areas within the blood vessel 102 where shape of the blood vessel 202 may be conical shaped.

It should be understood that the closed ends of the pair of lobes 214 may allow recapture of the vascular occlusion device 208 after deployment.

The body 210 may include a rod 226 that includes a distal end 220 and an opposite proximal end 222, and an adjustment assembly 224 positioned between. The distal end 220 may be distal of the adjustment assembly 224 and the proximal end 122 may be positioned between the proximal lobe 214b and the delivery assembly 206. As such, the delivery assembly 206 may be in contact with the proximal end 222 when the delivery assembly 206 is in contact with the body 210 of the vascular occlusion device 208. The distal end 220 may not extend beyond the distal lobe 214a. That is, the distal end 220 may terminate within the plurality of fibers 215 that form the distal lobe 214a. The rod 226 or catheter may extend between the proximal end 222 and the distal end 220 that define a length of the rod 226.

The adjustment assembly 224 may be positioned to extend axially between the pair of lobes 212. The adjustment assembly 224 may be configured to change a distance, or length, between the pair of lobes 212, as discussed in greater detail herein. In some embodiments, the adjustment assembly 224 may include a receiving member 256 and an elongated member 234. The receiving member 256 includes a first end 260a and an opposite second end 260b and an inner surface 257 that forms a cavity 258 extending between the first end 260a and the second end 260b. The cavity 258 receives the elongated member 234 in a retracted position, as illustrated best in FIGS. 6-7. As such, an outer surface 236 of the elongated member 234 is smaller than the diameter of the cavity 258. The elongated member 234 further includes a stop end 262a and an opposite lobe end 262b. The stop end 262a remains within the cavity 258 when the adjustment assembly 224 is in the extend position, as best illustrated in FIG. 8. Further, the proximal lobe 214b is attached or coupled to the lobe end 262b while the distal lobe 214a is coupled or attached to the first end 260a of the receiving member 256. The distal lobe 214a is coupled or attached to the first end 260a via a fastener such as a spot weld, adhesive, epoxy, hook and loop, screw, and/or the like. The proximal lobe 214b is attached or coupled to the lobe end 262b via a fastener such as a spot weld, adhesive, epoxy, hook and loop, screw, and/or the like.

The stop end 262a of the elongated member 234 may further include a protrusion 244 that extends radially outward from the outer surface 236. Further, a flange 242 may extend radially inward into the cavity 258 at, adjacent to, and/or near the second end 260b of the receiving member 256. The elongated member 234 may be configured to slidably move within the cavity 258 between the extended position, as shown in FIG. 8, and the retracted position, as best shown in FIGS. 6-7 via the catheter 216 of the deliver assembly 206. In other embodiments, it should be understood that there may be more than one elongated member that slidably moves within the cavity 258 and each additional elongated member may be telescoped within each other.

In the retracted position, the elongated member 234 may be received within the receiving member 256 such that the protrusion 244 is spaced apart from the flange 242 that the length of the elongated member 234. Alternatively, in the extended position, the elongated member 234 may extend within the cavity 258 of the receiving member 256 such that the second end 260b and the lobe end 262b are axially moved closer to one another until the protrusion 244 abuts the flange 242. It should be understood that the elongated member 234 may be configured to slidably move to a plurality of positions within the cavity 258 between the extended position and the retracted position and is only limited by the length of the elongated member 234 and the positioning of the protrusion 244 and/or the flange 242.

As such, when the elongated member 234 is moved to one of the plurality of positions within the cavity 258 between the extended position and the retracted position, the elongated member 234 may be held in that position removing the sheath 204 via the guidewire 205 to expand the proximal lobe 114b, thereby locking in the current length of the adjustment assembly 224.

Figures 10, 11, 12:
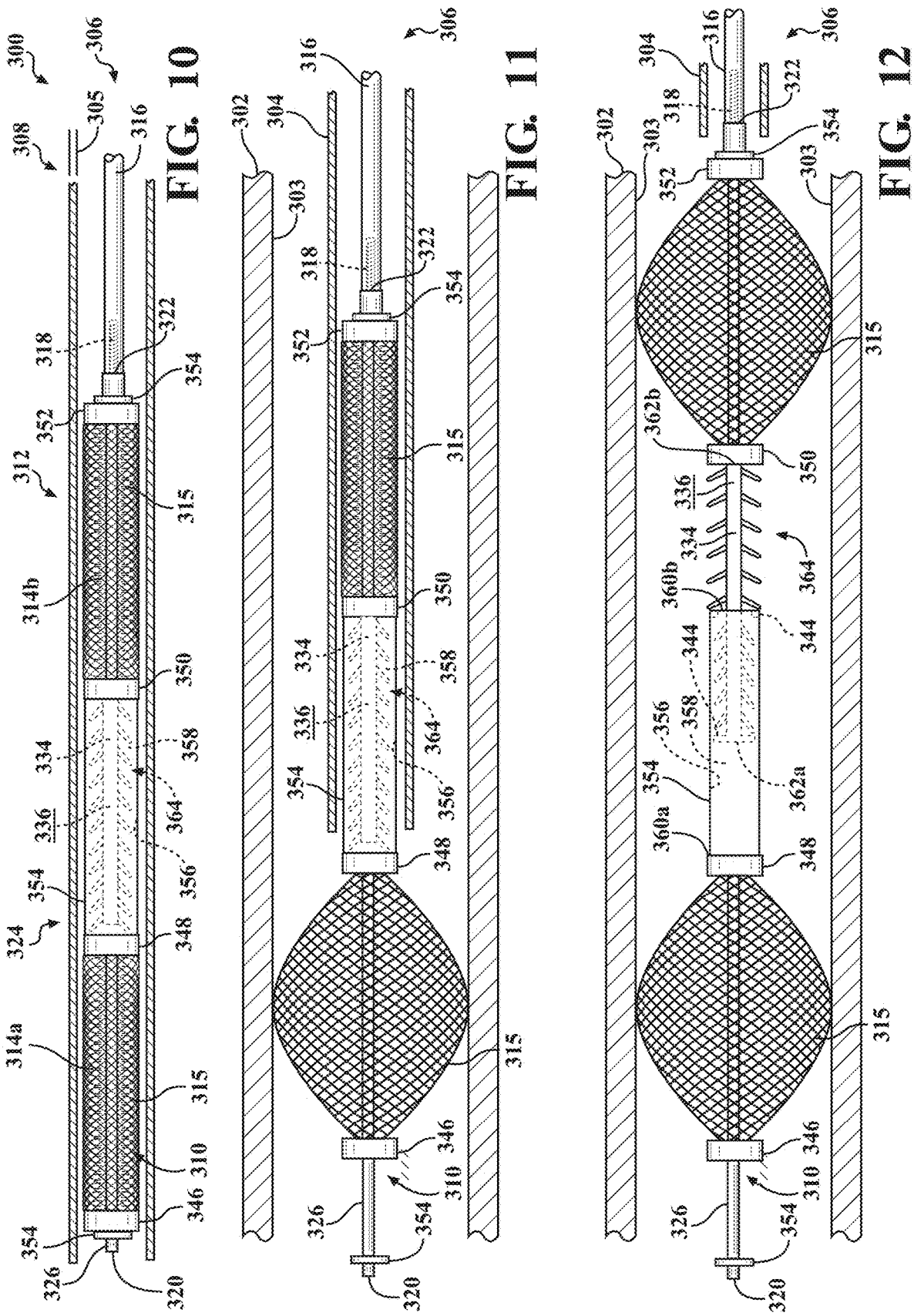
FIG. 10 schematically depicts a third aspect vascular occlusion device with a pair of lobes in a low profile configuration, according to one or more embodiments shown and described herein.
FIG. 11 schematically depicts the vascular occlusion device of FIG. 10 with one of the pair of lobes in a low profile configuration and the other lobe of the pair of lobes in a deployed configuration, according to one or more embodiments shown and described herein.
FIG. 12 schematically depicts the vascular occlusion device of FIG. 10 with the pair of lobes in the deployed configuration and the adjustment assembly in the extended position, according to one or more embodiments shown and described herein.

Now referring to FIGS. 10-12, a third embodiment of a vascular occlusion device 308 is schematically depicted. It is understood that the vascular occlusion device 308 is similar to the vascular occlusion device 108 with the exceptions of the features described herein. As such, like features will use the same reference numerals with a prefix "3" for the reference numbers. As such, for brevity reasons, these features will not be described again.

The body 310 may include rod 326 that includes a distal end 320 and an opposite proximal end 322, and an adjustment assembly 324 positioned between. The distal end 320 may be distal of the adjustment assembly 324 and the distal lobe 314a and the proximal end 322 may be positioned between the proximal lobe 314b and the delivery assembly 306. As such, the delivery assembly 306 may be in contact with the proximal end 322 when the delivery assembly 306 is in contact with the body 310 of the vascular occlusion device 308. The rod 326 or catheter may extend between the proximal end 322 and the distal end 320 that define a length of the rod 326. Further, in some embodiments, the distal end 320 and the proximal end 322 are cylindrical in shape to define a diameter along the length of the rod 326. In some embodiments, the rod 326 may have differential cross-section shapes other than circular, for example, rectangular, hexagonal, octagonal, and/or the like. Further, in some embodiments, the rod 326 may have a uniform shape between the proximal and distal ends 322, 320. In other embodiments, the rod 326 may be non-uniform or have irregular portions between the proximal and distal ends 322, 320.

The adjustment assembly 324 may be positioned to extend axially between the pair of lobes 312. The adjustment assembly 324 may be configured to change a distance between the pair of lobes 312, as discussed in greater detail herein. In some embodiments, the adjustment assembly 324 may incorporate a portion of the rod 326 and may further include a receiving member 354 and an elongated member 334. The receiving member 354 includes a first end 360a and an opposite second end 360b and an inner surface 356 that forms a cavity 358 extending between the first end 360a and the second end 360b. The cavity 358 receives the elongated member 334 in a retracted position, as illustrated best in FIGS. 9-10. As such, an outer surface 336 of the elongated member 334 is smaller than the diameter of the cavity 358. The elongated member 334 further includes a stop end 362a and an opposite lobe end 362b. The stop end 362a remains within the cavity 358 when the adjustment assembly 324 is in the extend position, as best illustrated in FIG. 11.

The stop end 362a of the elongated member 334 may further include a protrusion 344 that extends radially outward from the outer surface 336. Further, a plurality of resilient members 364 may extend radially outward from the outer surface 336 of the elongated member 334 and inward into the cavity 358. The elongated member 334 may be configured to slidably move within the cavity 358 between the extended position, as shown in FIG. 11, and the retracted position, as best shown in FIGS. 9-10 via the delivery assembly 306. The plurality of resilient members 364 may move from a folded positioned within the cavity 358, and as best illustrated in FIGS. 9-10, and an unfolded position, as best illustrated in FIG. 11. That is, each of the plurality of resilient members 364 may be a living hinge that permit movement between the folded positioned and the unfolded position, and vice versa, such that the adjustment assembly 324 may be repositionable between the extended position and the retracted position. Further, the plurality of resilient members 364, in the unfolded position, provide a friction to enable the length of the adjustment assembly 324 to be set and maintained by at least one of the plurality of resilient members 364 in the unfolded position in contact with the second end 360*b* of the receiving member 354.

In some embodiments, the plurality of resilient members 364 may be formed as a monolithic structure with the elongated member 334. As such, the plurality of resilient members 364 and the elongated member may be injection molded, three-dimensional printed, and/or the like. In other embodiments, the plurality of resilient members 364 may be attached to the outer surface 336 of the elongated member 334 via a fastener such as via weld, adhesive, epoxy, hook and loop, screws, and/or the like. The plurality of resilient members 364 may be any type of material that is moveable between the folded and unfolded position. For example, the plurality of resilient members 364 may comprise a plastic, such as a polypropylene material. In other embodiments, the resilient members 364 may comprise a self-expanding material, such as a Nitinol material.

In other embodiments, it should be understood that there may be more than one elongated member that slidably move within the cavity 358 and may be telescoped within each other.

Figures 13, 14:
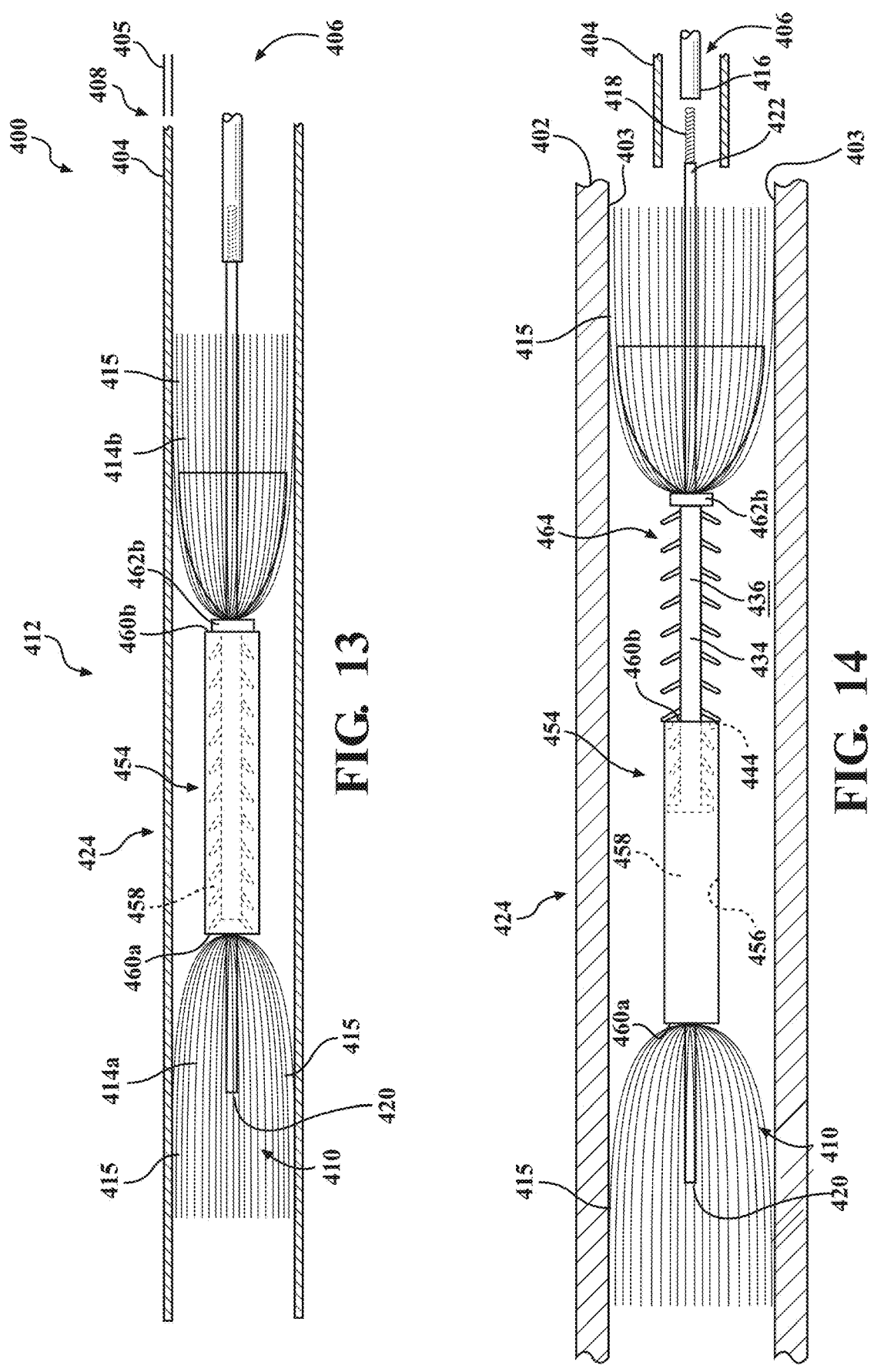
FIG. 13 schematically depicts a fourth aspect vascular occlusion device with a pair of lobes in a low profile configuration, according to one or more embodiments shown and described herein.
FIG. 14 schematically depicts the vascular occlusion device of FIG. 13 with the pair of lobes in the deployed configuration and the adjustment assembly in the extended position, according to one or more embodiments shown and described herein.

Now referring to FIGS. 13-14, a fourth embodiment of a vascular occlusion device 408 is schematically depicted. It is understood that the vascular occlusion device 408 is similar to the vascular occlusion device 208 with the exceptions of the features described herein. As such, like features will use the same reference numerals with a prefix "4" for the reference numbers. As such, for brevity reasons, these features will not be described again.

The adjustment assembly 424 may be positioned to extend axially between the pair of lobes 412. The adjustment assembly 424 may be configured to change a distance between the pair of lobes 412, as discussed in greater detail herein. In some embodiments, the adjustment assembly 424 may incorporate a portion of the rod 426 and may further include a receiving member 454 and an elongated member 434. The receiving member 454 includes a first end 460*a* and an opposite second end 460*b* and an inner surface 456 that forms a cavity 458 extending between the first end 460*a* and the second end 460*b*. The cavity 458 receives the elongated member 434 in a retracted position, as illustrated best in FIG. 12. As such, an outer surface 436 of the elongated member 434 is smaller than the diameter of the cavity 458. The elongated member 434 further includes a stop end 462*a* and an opposite lobe end 462*b*. The stop end 462*a* remains within the cavity 458 when the adjustment assembly 424 is in the extend position, as best illustrated in FIG. 13.

The stop end 462*a* of the elongated member 434 may further include a protrusion 444 that extends radially outward from the outer surface 436. Further, a plurality of resilient members 464 may extend radially outward and from the outer surface 436 of the elongated member 434 and angled distally (e.g., inward) into the cavity 458. The plurality of resilient members 464 may be shaped as spikes, as cantilevered beams, and/or the like. The elongated member 434 may be configured to slidably move within the cavity 458 between the extended position, as shown in FIG. 13, and the retracted position, as best shown in FIG. 12 via the delivery assembly 406. The plurality of resilient members 464 may move from a folded positioned within the cavity 458, and as best illustrated in FIG. 12, and an unfolded position, as best illustrated in FIG. 13. That is, each of the plurality of resilient members 464 may be a living hinge that permit movement between the folded positioned and the unfolded position, and vice versa, such that the adjustment assembly 424 may be repositionable between the extended position and the retracted position. Further, the plurality of resilient members 464, in the unfolded position, provide a friction to enable the length of the adjustment assembly 424 to be set and maintained by at least one of the plurality of resilient members 464 in the unfolded position in contact with the second end 460*b* of the receiving member 454.

In some embodiments, the plurality of resilient members 464 may be formed as a monolithic structure with the elongated member 434. As such, the plurality of resilient members 464 and the elongated member may be injection molded, three-dimensional printed, and/or the like. In other embodiments, the plurality of resilient members 464 may be attached to the outer surface 436 of the elongated member 434 via a fastener such as via weld, adhesive, epoxy, hook and loop, screws, and/or the like. The plurality of resilient members 464 may be any type of material that is moveable between the folded and unfolded position. For example, the plurality of resilient members 464 may comprise a plastic, such as a polypropylene material. In other embodiments, the resilient members 464 may comprise a self-expanding material, such as a Nitinol material.

In other embodiments, it should be understood that there may be more than one elongated member that slidably move within the cavity 458 and may be telescoped within each other.

Embodiments of the present disclosure may be further described with respect to the following numbered clauses:

1. An occlusion device comprising a body, a pair of lobes, and an adjustment assembly. The body having a distal portion and a proximal portion. One of the pair of lobes is positioned at the distal portion of the body and the other one of the pair of lobes is positioned at the proximal portion of the body. The body comprising an adjustment assembly positioned between the pair of lobes to change a distance between the pair of lobes. The adjustment assembly includes a receiving member and an elongated member. The receiving member includes a first end, an opposite second end and an inner diameter. The second end has a flange that extends radially inward into the inner diameter. The elongated member includes a first terminating end, an opposing second terminating end and an outer diameter. The first terminating end has a protrusion that extends radially outward from the outer diameter. The elongated member is configured to move the body between an extended position and a retracted position, such that in the retracted position, the elongated member is received within the inner diameter of the receiving member such that the protrusion is spaced apart from the flange. In the extended position, the elongated member is extended away from the first end of the receiving member such that the second end of the receiving member and the first terminating end of the elongated member are adjacent and the protrusion abuts the flange such that the distance between the pair of lobes is increased.

2. The occlusion device of clause 1, wherein the adjustment assembly further comprises: one or more resilient members extending outwardly from an outer surface of the elongated member between the first terminating end and the second terminating end of the elongated member, wherein in the retracted position, the one or more resilient members are received within the inner diameter of the receiving member and in the extended position, at least one of the one or more resilient members is extended from the outer diameter of the elongated member to abut second end of the receiving member such that the distance between the pair of lobes is increased and locked.

3. The occlusion device of any preceding clause, wherein in the extended position, the elongated member is repositionable from the extended position to the retracted position.

4. The occlusion device of any preceding clause, wherein the pair of lobes configured to cause embolization of a blood vessel.

5. The occlusion device of any preceding clause, wherein each lobe of the pair of lobes are shaped to circumferentially contact a vessel wall of the blood vessel to occlude the blood vessel.

6. The occlusion device of any preceding clause, wherein each lobe of the pair of lobes are self-expanding to extend between a low profile configuration to a deployed configuration to circumferentially contact a diameter of the blood vessel.

7. The occlusion device of any preceding clause, wherein each lobe of the pair of lobes comprises a Nitinol® fiber material.

8. The occlusion device of any preceding clause, wherein each lobe of the pair of lobes comprise a metal mesh material.

9. The occlusion device of any preceding clause, wherein the body comprises a radiopaque material.

10. The occlusion device of any preceding clause, wherein the proximal end of the body is releasably coupled to a guide wire delivery device.

11. An occlusion device configured to cause embolization of a blood vessel comprising a body, a pair of lobes, and an adjustment assembly. The body includes a distal portion and a proximal portion. One of the pair of lobes is positioned at the distal portion of the body and the other one of the pair of lobes is positioned at the proximal portion of the body. Each lobe of the pair of lobes is shaped to circumferentially contact a vessel wall of the blood vessel to occlude the blood vessel. The body comprising an adjustment assembly positioned between the distal portion and the proximal portion to change a distance between the pair of lobes. The adjustment assembly includes a receiving member and an elongated member. The receiving member has a first end, a second end and an inner diameter. The second end has a flange that extends radially inward into the inner diameter. The elongated member has a first terminating end, a second terminating end, and an outer diameter. The first terminating end having a protrusion that extends radially outward from the outer diameter. The elongated member is configured to move the body between an extended position and a retracted position, such that in the retracted position, the elongated member is received within the inner diameter of the receiving member such that the protrusion is spaced apart from the flange. In the extended position, the elongated member is extended away from the first end of the receiving member such that the second end of the receiving member and the first terminating end of the elongated member are adjacent and the protrusion abuts the flange such that the distance between the pair of lobes is increased.

12. The occlusion device of any preceding clause, wherein the adjustment assembly further comprises: one or more resilient members extend outwardly between the first terminating end and the second terminating end of the elongated member, wherein in the retracted position, the one or more resilient members are received within the inner diameter of the receiving member and in the extended position, at least one of the one or more resilient members is extended from the outer diameter of the elongated member to abut second end of the receiving member such that the distance between the pair of lobes is increased and locked.

13. The occlusion device of any preceding clause, wherein the pair of lobes and the body are coaxial aligned.

14. The occlusion device of any preceding clause, wherein each lobe of the pair of lobes are self-expanding to extend between a low profile configuration to a deployed configuration to circumferentially contact a diameter of the blood vessel.

15. The occlusion device of any preceding clause, wherein each lobe of the pair of lobes comprise a metal mesh material.

16. The occlusion device of any preceding clause, wherein each lobe of the pair of lobes comprise a Nitinol® fiber material.

17. The occlusion device of any preceding clause, wherein the body comprises a radiopaque material.

18. The occlusion device of any preceding clause, wherein the proximal end of the body is releasably coupled to a guide wire delivery device.

19. A method for embolization of a blood vessel, the method comprising: inserting, by a delivery device, an occlusion device into the blood vessel, the occlusion device having a body and a pair of lobes, the body has a distal portion and a proximal portion, one of the pair of lobes is positioned at the distal portion of the body and the other one of the pair of lobes is positioned at the proximal portion of the body; positioning the occlusion device at a target location; deploying one of the pair of lobes within the blood vessel such that the one of the pair of lobes circumferentially contact a diameter of the blood vessel to provide a radial force for stability at the target location; adjusting a distance between the pair of lobes of the occlusion device via an adjustment assembly such that the pair of lobes are positioned on either side of the target location; and deploying the other one of the pair of lobes within the blood vessel such that the pair of lobes circumferentially contact the diameter of the blood vessel to inhibit a blood flow at the target location and to provide the radial force for stability at the target location.

20. The method of any preceding clause, wherein each lobe of the pair of lobes comprise a metal mesh material, a Nitinol® fiber material, or a combination thereof.

It should now be appreciated that embodiments described herein relate to an occlusion device that includes a body that may be adjustable, connecting a pair of lobes for embolization of peripheral vasculature. The pair of lobes may be a self-expanding metallic mesh, Nitinol fibers segments, and/or the like. The pair of lobes may inhibit blood flow and may expand to match the diameter of the vessel, providing sufficient radial force for stability at a target location. The body includes various adjustable devices that allow the body to move between an extended position and a retracted position. The retracted position is the minimum space between the pair of lobes. The extended position is a largest gap, or space, between the pair of lobes. As such, the body increases a length of the occlusion device to a desired length.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An occlusion device comprising:
    a body having a distal portion and a proximal portion;
    a pair of lobes, one of the pair of lobes is positioned at the distal portion of the body and the other one of the pair of lobes is positioned at the proximal portion of the body; and
    an adjustment assembly positioned between the distal portion and the proximal portion of the body and integrated within the body to change a distance between the pair of lobes, the adjustment assembly having:
        a receiving member having a first end, an opposite second end, and an inner diameter, the second end having a flange that extends radially inward into the inner diameter; and
        an elongated member having a first terminating end, an opposing second terminating end, and an outer diameter, the first terminating end having a protrusion that extends radially outward from the outer diameter,
        wherein the elongated member is configured to move the body between an extended position and a retracted position, such that in the retracted position, the elongated member is received within the inner diameter of the receiving member such that the protrusion is spaced apart from the flange, and in the extended position, the elongated member is extended away from the first end of the receiving member such that the second end of the receiving member and the first terminating end of the elongated member are adjacent and the protrusion abuts the flange such that the distance between the pair of lobes is increased.

2. The occlusion device of claim 1, wherein the adjustment assembly further comprises:
    one or more resilient members extending outwardly from an outer surface of the elongated member between the first terminating end and the second terminating end of the elongated member,
    wherein in the retracted position, the one or more resilient members are received within the inner diameter of the receiving member and in the extended position, at least one of the one or more resilient members is extended from the outer diameter of the elongated member to abut second end of the receiving member such that the distance between the pair of lobes is increased and locked.

3. The occlusion device of claim 1, wherein in the extended position, the elongated member is repositionable from the extended position to the retracted position.

4. The occlusion device of claim 1, wherein the pair of lobes are configured to occlude flow through a blood vessel.

5. The occlusion device of claim 4, wherein each lobe of the pair of lobes are shaped to circumferentially contact a vessel wall of the blood vessel to occlude the blood vessel.

6. The occlusion device of claim 5, wherein each lobe of the pair of lobes are self-expanding to extend between a low profile configuration to a deployed configuration to circumferentially contact a diameter of the blood vessel.

7. The occlusion device of claim 6, wherein each lobe of the pair of lobes comprises a Nitinol® fiber material.

8. The occlusion device of claim 6, wherein each lobe of the pair of lobes comprise a metal mesh material.

9. The occlusion device of claim 1, wherein the body comprises a radiopaque material.

10. The occlusion device of claim 1, wherein the proximal end of the body is releasably coupled to a guide wire delivery device.

11. An occlusion device configured to cause embolization of a blood vessel, the occlusion device comprising:
    a body having a distal portion and a proximal portion;
    a pair of lobes, one of the pair of lobes is positioned at the distal portion of the body and the other one of the pair of lobes is positioned at the proximal portion of the body, each lobe of the pair of lobes is shaped to circumferentially contact a vessel wall of the blood vessel to occlude the blood vessel; and
    the body comprising an adjustment assembly positioned between the distal portion and the proximal portion to change a distance between the pair of lobes, the adjustment assembly having:
        a receiving member having a first end, a second end, and an inner diameter, the second end having a flange that extends radially inward into the inner diameter; and
        an elongated member having a first terminating end, an opposite second terminating end, and an outer diameter, the first terminating end having a protrusion that extends radially outward from the outer diameter,
        wherein the elongated member is configured to move the body between an extended position and a retracted position, such that in the retracted position, the elongated member is received within the inner diameter of the receiving member such that the protrusion is spaced apart from the flange, and in the extended position, the elongated member is extended away from the first end of the receiving member such that the second end of the receiving member and the first terminating end of the elongated member are adjacent and the protrusion abuts the flange such that the distance between the pair of lobes is increased.

12. The occlusion device of claim 11, wherein the adjustment assembly further comprises:
    one or more resilient members extending outwardly between the first end and the second end of the elongated member,
    wherein in the retracted position, the one or more resilient members are received within the inner diameter of the receiving member and in the extended position, at least one of the one or more resilient members is extended from the outer diameter of the elongated member to abut second end of the receiving member such that the distance between the pair of lobes is increased and locked.

13. The occlusion device of claim 11, wherein the pair of lobes and the body are coaxially aligned.

14. The occlusion device of claim 13, wherein each lobe of the pair of lobe s comprise a metal mesh material.

15. The occlusion device of claim 13, wherein each lobe of the pair of lobes comprise a Nitinol® fiber material.

16. The occlusion device of claim 11, wherein each lobe of the pair of lobes are self-expanding to extend between a low profile configuration to a deployed configuration to circumferentially contact a diameter of the blood vessel.

17. The occlusion device of claim 11, wherein the body comprises a radiopaque material.

18. The occlusion device of claim 11, wherein the proximal end of the body is releasably coupled to a guide wire delivery device.

19. A method for embolization of a blood vessel, the method comprising:

inserting, by a delivery device, an occlusion device into the blood vessel, the occlusion device having a body and a pair of lobes, the body has a distal portion and a proximal portion, one of the pair of lobes is positioned at the distal portion of the body and the other one of the pair of lobes is positioned at the proximal portion of the body;

positioning the occlusion device at a target location;

deploying one of the pair of lobes within the blood vessel such that the one of the pair of lobes circumferentially contact a diameter of the blood vessel to provide a radial force for stability at the target location;

adjusting a distance between the pair of lobes of the occlusion device via an adjustment assembly such that the pair of lobes are positioned on either side of the target location; and deploying the other one of the pair of lobe s within the blood vessel such that the pair of lobes circumferentially contact the diameter of the blood vessel to inhibit a blood flow at the target location and to provide the radial force for stability at the target location.

20. The method of claim 19, wherein each lobe of the pair of lobes comprise a metal mesh material, a Nitinol® fiber material, or a combination thereof.

\* \* \* \* \*